US012799043B2

(12) United States Patent
Nakas

(10) Patent No.: US 12,799,043 B2
(45) Date of Patent: Nov. 17, 2026

(54) MICROBIOLOGICAL METHOD OF NITRIFICATION FOR PRODUCTION OF ORGANIC FERTILIZERS

(71) Applicant: UAB AGRICHEM INNOVATION, Vilnius (LT)

(72) Inventor: Tomas Nakas, Vilnius (LT)

(73) Assignee: UAB AGRICHEM INNOVATION, Vilnius (LT)

( * ) Notice: Subject to any disclaimer, the term of this patent is extended or adjusted under 35 U.S.C. 154(b) by 185 days.

(21) Appl. No.: 18/880,128

(22) PCT Filed: Jun. 9, 2023

(86) PCT No.: PCT/IB2023/055961

§ 371 (c)(1),
(2) Date: Dec. 30, 2024

(87) PCT Pub. No.: WO2024/003639

PCT Pub. Date: Jan. 4, 2024

(65) Prior Publication Data

US 2025/0382238 A1 Dec. 18, 2025

(30) Foreign Application Priority Data

Jul. 1, 2022 (LT) ...................................... 2022527

(51) Int. Cl.

| | |
|---|---|
| ***C05C 5/02*** | (2006.01) |
| ***C01D 9/04*** | (2006.01) |
| ***C01F 11/38*** | (2006.01) |
| ***C05C 5/04*** | (2006.01) |
| ***C12P 3/00*** | (2006.01) |

(52) U.S. Cl.
CPC .................. *C05C 5/02* (2013.01); *C01D 9/04* (2013.01); *C01F 11/38* (2013.01); *C05C 5/04* (2013.01); *C12P 3/00* (2013.01)

(58) Field of Classification Search
CPC .. C05C 5/02; C05C 5/04; C05C 11/00; C01D 9/04; C01F 11/38; C12P 3/00; C05F 11/08; C05F 17/10; C05F 17/20; C05F 3/00
See application file for complete search history.

(56) References Cited

U.S. PATENT DOCUMENTS

| | | | |
|---|---|---|---|
| 11,358,096 | B2 | 6/2022 | Van Wakeren et al. |
| 2020/0061534 | A1 | 2/2020 | Van Wakeren et al. |

FOREIGN PATENT DOCUMENTS

| | | | |
|---|---|---|---|
| WO | 2007097612 | A2 | 8/2007 |

OTHER PUBLICATIONS

International Search Report issued in corresponding PCT Application No. PCT/IB2023/055961 dated Oct. 10, 2023, 4 pgs.

*Primary Examiner* — Paul J Holland
(74) *Attorney, Agent, or Firm* — Tutunjian & Bitetto, P.C.

(57) ABSTRACT

The aim of the present invention is to provide a liquid or crystallized form of NPK fertilizer based on nitrate nitrogen, which is obtained on the basis of organic chemistry, from recycling agricultural and industrial wastes and waste materials through an organic microbiological nitrification process. Products such as potassium nitrate, magnesium nitrate, iron nitrate, and calcium nitrate produced in this way become environmentally friendly products.

7 Claims, 2 Drawing Sheets

Specification includes a Sequence Listing.

MICROBIOLOGICAL METHOD OF NITRIFICATION FOR PRODUCTION OF ORGANIC FERTILIZERS

FIELD OF THE INVENTION

The invention is related to the production of organic NPK fertilizers, wherein nitrogen of ammonia (NH3) is processed using the microbiological nitrification method by oxidizing ammonia into nitrate nitrogen (N—NOs-) salts, with the simultaneous use of natural alkaline elements in the process. More precisely, using ammonia nitrogen gas (N—NH3 and/or N—NH4) or their compounds of animal origin or obtained by the method of raw hydrogen production for extraction and binding of ammonia gas (NH3) in a solution with plant-derived carbon dioxide (CO2) gas; also, to oxidize the prepared solution of ammonia nitrogen ($NH4^+$) by means of microbiological nitrification with the participation of genera of microorganisms (groups of archaea and bacteria) such as *Nitrosomonas, Nitrosococcus*, and Nitrospira, as well as using castes, plant or animal origin alkali metal $K^+$, $Ca^{2+}$, $Mg^{2+}$, and metal $Fe^{2+}$ element compounds in the process. The obtained solutions of nitrate nitrogen are concentrated, salts are crystallized from them, and thus organic NPK fertilizers are prepared.

STATE OF THE ART

The special conditions of the solution within the intended capacity of the production process are controlled and maintained with the help of a computer control program and the necessary sensors. Nitrifying genera of microorganisms, such as *Nitrosomonas* and Nitrospira, oxidize ammonia (NH3) gas of animal origin or extracted from raw hydrogen production to nitrate nitrogen (N—NOs-) salts. Also, the production solution is maintained at the required temperature and it is supplied with dissolved oxygen and alkaline potassium, calcium, magnesium, or iron ions, thus ensuring that the solution maintains a balance of positive and negative ions and a stable pH level.

Organic NPK fertilizers, based on nitrate nitrogen, are obtained from natural raw materials, are not inferior in efficiency, and have the same elemental composition and concentration levels as mineral fertilizers. In the organic food industry, most organic fertilizers are based on organic nitrogen, which cannot be assimilated by the plant. The organic food industry also uses manure of animal origin, dominated by ammonia and nitrate nitrogen but containing pathogens and emitting odor. If animal manure can be incorporated into the soil, liquid manure may not be applied for hydroponic, aeroponic, irrigation, or spray crop production because ammoniacal nitrogen ions become toxic to the plant under certain conditions, giving the crop an unpleasant smell and contaminating food with harmful pathogens.

The aim of this invention is to use the ammonia nitrogen waste from animal breeding farms and animal manure processing companies as natural ammonia gas, to convert it into safe organic fertilizers, and to bring it back to the market in the form of a product according to the green economic principle. Manufactured organic nitrate nitrogen NPK fertilizers are delivered in safe, stable salt forms where they are most needed: in greenhouses, foliar spraying of crops, and in irrigation water supply systems.

The closest prior art, US2020061534, describes the capture of ammonia gas in farms and biogas air scrubbers by means of water and carbon dioxide (CO2) gas, but the method is not efficient because the chemical compound ammonium bicarbonate ($NH_4HCO_3$) formed in the air scrubbers is in the form of unstable salts in water, and when the temperature reaches +35 °C degrees and above, due to the warm air leaving farms or hot ambient air, this salt compound breaks down into ammonia (NH3) and carbon dioxide (CO2) gases and starts to evaporate into the atmosphere.

This invention helps simplify the management of ammonia (NH3) gas because ammonia (NH3) gas is extracted from ammoniacal nitrogen compounds according to the rules of organic chemistry and is bound with plant-derived carbon dioxide (CO2) in a special container with an aqueous solution, thus allowing the ammonium bicarbonate ($NH_4HCO_3$) compound to remain stable and not evaporate. Ammonium bicarbonate can be used in the production of nitrate nitrogen salts.

BRIEF DESCRIPTION OF THE INVENTION

The aim of the invention is to provide organic NPK fertilizers in liquid or crystallized form, which are produced by microbiological nitrification. Organic products such as potassium nitrate, magnesium nitrate, calcium nitrate and iron nitrate are produced from organic waste by using agricultural waste containing ammonia nitrogen (ammonia (NH3) gas, ammonia nitrogen (NH4+) solutions collected from farms; during biogas production; in composting and manure processing plants captured with the help of ventilation filtration systems, in air scrubbers; ammonia gas obtained by the method of green hydrogen production; or from renewable energy sources), ash of plant and animal origin (waste can be ash of plants, their parts or wood; animal manure or litter ash) or compounds of natural caste raw materials containing potassium, calcium, iron or magnesium elements.

The present invention describes ammonia (NH3) gas of animal origin, compounds of ammonia nitrogen (NH4+) as agricultural and industrial wastes obtained from raw hydrogen production or produced from renewable sources, and ammonia (NH3) gas, wherein compounds are captured with synthetic or organic materials and recycled. Ammonia gas is extracted from ammonia nitrogen compounds by the extraction method, and the gas is transferred to another solution to form an organic compound according to the rules of organic chemistry with natural carbon dioxide gas. The microbiological method of nitrification used includes the following steps:

(A) supplying animal-derived ammonia nitrogen in the form of compounds, introducing an alkaline ingredient to produce ammonia in gaseous form, reacting ammonia gas with carbon dioxide (CO2) gas to produce an ammonium bicarbonate solution, and feeding it to a microbiological nitrification reactor;

(B) passing ammonia gas through a reactor that includes groups of archaea and bacteria present in the water, (C) injecting alkaline element salts and oxygen into the reactor, (D) obtaining a solution of nitrate nitrogen and an alkaline element, (E) concentration of nitrate nitrogen and alkali element solution, and (F) crystallization of nitrate nitrogen and salts of an alkaline element.

Compounds containing $Ca^{2+}$, $Fe^{2+}$, $Mg^{2+}$, and $K^+$ ions, such as iron oxide or iron carbonate compound, calcium oxide or calcium carbonate compound, magnesium carbonate, magnesium sulfate, magnesium chloride, and potassium carbonate, are used as raw materials.

In the microbial nutrification process, ammonia gas is passed through the reactor that contains archaea and bacteria in its water selected from the *Nitrosomonas, Nitrosococcus*, and *Nitrobacter* groups. Specifically, the following strains were used: Strain 1: *Nitrosomonas aestuarii*, ATCC PTA-5423, deposited in the American Type Culture Collection, Strain 2*: Nitrosococcus oceani* ATCC 19707, deposited in the American Type Culture Collection, Strain 3: *Nitrobacter* wi nog rads kyi, ATCC 25391, deposited in the American Type Culture Collection.

The pH value of the nitrification process solution is maintained in a range of 5.9 to 8.0, depending on the type of alkaline element that is present in the solution, which forms salts with nitrate nitrogen ions. The temperature of the reactor solution is maintained between +18 °C and +30 °C, depending on the required speed of the nitrification process. The concentration of the ammonium sulfate solution formed in step (A) is between 5 and 15% of salt.

In order to control and manage the entire nitrification process, a set of sensors and a control module are additionally installed.

DETAILED DESCRIPTION OF THE INVENTION

Organic NPK fertilizers based on nitrate nitrogen obtained by the method of the present invention ensure more efficient plant growth and higher yields in organic farming. The safe and pathogen-free organic NPK fertilizers based on this invention allow them to be used in all cultivation systems for all vegetable and fruit crops, as well as for plants with a particularly short vegetation period, such as lettuce, dill, bulbs or their leaves, microgreens, and the like.

Ammonia (NH3) Gas Extraction and Preparation of the Solution for the Microbiological Nitrification Process Organic NPK fertilizers are produced using natural ammonia (NH3) gases of animal origin, collected from agricultural farms air purification systems, during the production processes of biogas, and in the production processes of manure composting and processing. Ammonia (NH3) gas is usually combined with sulfuric acid ($H_2SO_4$) to produce and collect a liquid solution of ammonium sulfate $(NH_4)_2SO_4$, which has salt concentrations of between 5 and 15% as a standard and is an agricultural waste.

Figure 1:
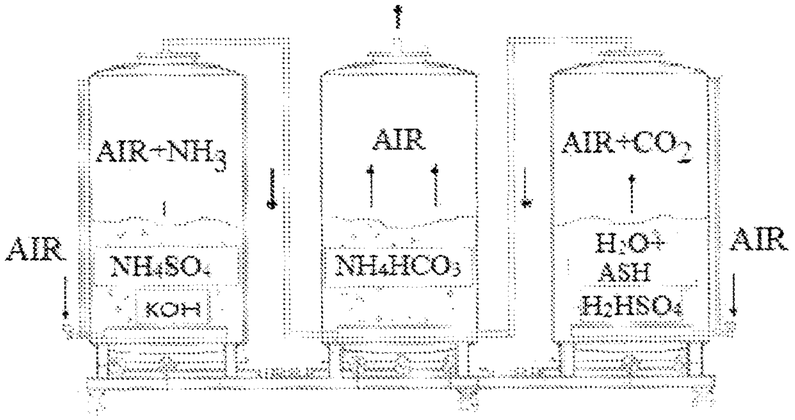
FIG. 1: Gas extraction and preparation of the solution for the microbiological nitrification process.

Subsequently, the ammonium sulfate $(NH_4)_2SO_4$ solution is poured into a sealed container into which an alkaline ingredient (sodium hydroxide, potassium hydroxide, calcium oxide, etc.) is continuously added at a constant rate until the pH of the solution reaches a pH value of 10-12. After evaporation from the alkaline solution, ammonia ($NH_3$) gas is sucked out by a compressor and piped to another tank containing water, which is saturated with carbon dioxide (CO2) gas (FIG. 1).

Carbon Dioxide (CO2) Gas Extraction and Preparation of the Solution for the Microbiological Nitrification Process Organic NPK fertilizers are produced using naturally occurring carbon dioxide (CO2) gas extracted from ash or caste raw materials of plant or animal origin, dominated by oxides of alkaline elements and carbonate (CO3) ionic compounds. Ashes of vegetable and animal origin are collected from urban boiler houses, oil factories, and similar industries where plants and their parts or wood waste are used in the combustion process. The treatment of any acid with carbonate (CO3) compounds, either from the waste from this industry or from calcium or magnesium rocks containing carbonate (CO3) compounds, produces the carbon dioxide (CO2) gases needed for the process.

After mixing water and ash in a special container, an acidic ingredient (vinegar, citric acid, sulfuric acid, etc.) is constantly added to the solution until the pH of the solution reaches a pH of 3-4. After evaporation from the acid solution, carbon dioxide (CO2) gas is sucked out by a compressor and piped to another tank containing water, which is saturated with ammonia (NH3) gas (FIG. 1).

Preparation of Alkali Metal $Ca^{2+}$, $Mg^{2+}$, $K^+$, and metal $Fe^{2+}$ Cations for Microbiological Processes When the powdered caste, agricultural, or industrial waste arrives at the production premises, it is mixed with water in a special container under constant agitation. After a period of time, the water-insoluble salts are allowed to settle in the water after the stirring has stopped, and the dissolved salts are washed away with the water and are used in the microbiological process of nitrification.

The sourcing and use of each raw material are shown below:

A compound of iron oxide ($FeO^+$) or iron carbonate (FeCOs), as an alkaline element, is collected as waste in municipal water treatment systems as part of a de-ironing process in which the waste to be disposed of is based on iron oxide. Cast iron ore is rock in the form of iron oxide ($FeO^+$) or iron carbonate (FeCOs).

The source of calcium oxide ($CaO^+$) or calcium carbonate (CaCOs) is industrial agroincinerated waste of industrial agro-plant and animal origin based on insoluble or sparingly soluble compounds of calcium oxide and calcium carbonate, which are washed with water and separated from insoluble sediments. Cast calcium carbonate (CaCOs) or calcium oxide ($CaO^+$) in the form of chalk, calcite, shell flour, or limestone is also used.

Cast magnesium carbonate (MgCOs), magnesium sulfate ($MgS0_4$), and magnesium chloride (MgCl2) are used as a source of magnesium ($Mg^{2+}$), which, after processing, are then used to extract the source of magnesium hydroxide $Mg(OH)_2$.

The source of potassium ($K^+$) is soluble, water-washed salts. The use of vegetable ash, in which the soluble salts of potassium are in the form of a carbonate compound (K2CO3), separates the salts dissolved in water from the insoluble sediment.

The Microbiological Process of Nitrification

Figure 2:
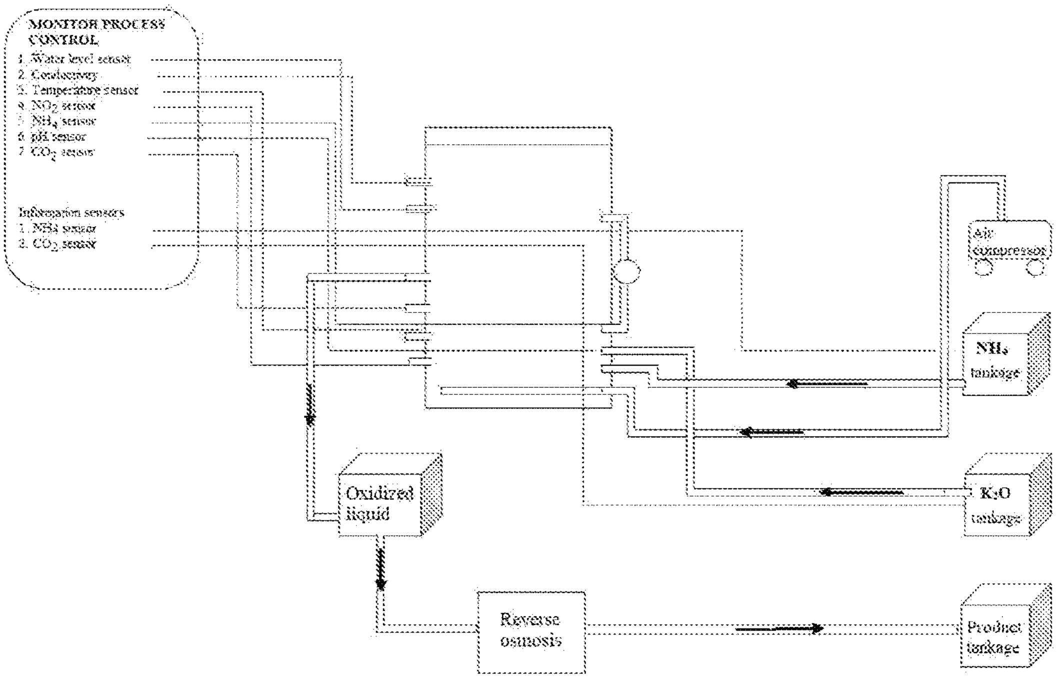
FIG. 2: Schematic diagram of the microbial nitrification process.

The microbiological process of nitrification takes place in a tank, a microbiological reactor (FIG. 2). It is a sealed water tank filled with water and the necessary microorganisms, such as *Nitrosomonas, Nitrosococcus*, and *Nitrobacter* groups of archaea and bacteria. In addition, a set of required sensors is installed, and automated process control software is used.

The automated process control program uses sensors to control the conditions in the microbiological reactor for the nitrification process, which are necessary to maintain the life of the microorganisms and carry out the oxidation of ammonia nitrogen. An automated control system maintains the concentration of nitrate nitrogen (N—$NO^{3-}$) ions in the microbiological reactor solution up to 0.8%. The pH of the solution from the nitrification process is monitored in the range 5.9 to 8.0, depending on the type of alkaline element present in the solution, which forms salts with nitrate nitrogen ions. The temperature of the reactor solution is maintained between +18 °C and +30 °C, depending on the required rate of the nitrification process. The reactor control program uses sensors to steadily inject the required substances, such as ammoniacal nitrogen solution, alkaline element solution, and oxygen, into the nitrification process solution, depending on the biochemical process conditions.

During the nutrification process, the *Nitrosomonas* group of archaea and bacteria oxidize ammonia nitrogen ions in the solution to nitrite nitrogen (NO2') ions according to the following reaction:

$$N\,H4^{+}\,(aq) + {}^{3}/2\ 02(g) \longrightarrow NO2'(aq) + 2H^{+}(aq) + H2O(I)$$

The *Nitrobacter* group of archaea and bacteria further oxidizes nitrite nitrogen (NO2') ions in solution to nitrate nitrogen (NOs-) ions according to the following reaction:

$$NO2(aq) + {}^{1}/2\ 02(g) \longrightarrow NO3'(aq)$$

Preparation of Liquid Organic Fertilizers Such as Potassium Nitrate, Magnesium Nitrate, Iron or Calcium Nitrate The resulting nitrate-nitrogen-based fertilizer solution, such as calcium nitrate, magnesium nitrate, iron nitrate, or potassium nitrate, is poured into a storage tank, from which it is then fed to a molecular sieve concentrator. In the concentration device, excess water is removed, and the content of salts in the product solution increases up to 3.75 times. T The final product is an organic liquid NPK fertilizer with a concentration of 3% nitrate nitrogen, which is then dispensed into the required containers.

Crystallization of Potassium Nitrate, Magnesium Nitrate, Iron Nitrate, or Calcium Nitrate Concentrated organic liquid NPK fertilizers such as potassium nitrate (NPK 3-0-9+K), calcium nitrate (NPK 3-0-0+Ca), magnesium nitrate (NPK 3-0-0+Mg), or iron nitrate (NPK 3-0-0+Fe) are cooled to a temperature in the range of −5 °C to 0 °C, and the salt crystallization process takes place in the solution. After decanting or centrifuging the solution from the formed salts, the latter is returned to the concentrating stage, and the resulting crystallized salts, such as potassium nitrate (NPK 13-0-46), calcium nitrate (NPK 16-0-0+Ca), magnesium nitrate (NPK 11-0-0+Mg) with a nitrogen concentration of 13-18% are packaged.

The invention claimed is:

1. A microbiological nitrification method for the production of organic fertilizers by oxidizing ammonia to nitrate nitrogen salts, which is characterized in that this method comprises the following steps:

(A) supplying animal-derived ammonia nitrogen in the form of compounds, wherein ammonia gas is combined with sulfuric acid to produce a liquid solution of ammonium sulfate, which is mixed with an alkaline ingredient at pH of 10-12 to produce ammonia gas, B) injecting of ammonia in gaseous or liquid state to a microbial nitrification reactor and passing through a reactor that includes groups of archaea and bacteria present in the water, (C) injecting alkali element salts and oxygen into the reactor, (D) obtaining a solution of nitrate nitrogen and an alkaline element, (E) concentrating the solution of nitrate nitrogen and the alkaline element, and (F) crystallizing of salts of nitrate nitrogen and the alkaline element.

2. A microbiological nitrification method for the production of organic fertilizers by oxidizing ammonia to nitrate nitrogen salts according to claim 1, wherein liquid state of step (B) is obtained by binding ammonia gas to carbon dioxide (CO2) gas produce an ammonium bicarbonate solution.

3. The method for the fixation of ammonia (NH3) gas or ammoniacal nitrogen (NH4+) compounds from organic waste according to claim 1, wherein the elements are selected from the alkali metals $Ca^2$+, $Mg^2$+, K+, and the metal $Fe^2$+ cations.

4. The method for the fixation of ammonia (NH3) gas or ammoniacal nitrogen (NH4+) from organic waste according to claim 1, wherein the group of archaea and bacteria is selected from the *Nitrosomonas, Nitrosococcus*, and *Nitrobacter.*

5. The method for the fixation of ammonia (NH3) gas or ammoniacal nitrogen (NH4+) from organic waste according to claim 1, wherein the pH of the nitrate nitrogen solution is in the range of 5.9 to 8.0.

6. The method for the fixation of ammonia (NH3) gas or ammonia nitrogen (NH4+) from organic waste according to claim 1, wherein the concentration of the ammonium sulfate solution formed in step (A) is from 5 to 15% salts.

7. The method for the fixation of ammonia (NH3) gas or ammoniacal nitrogen (NH4+) from organic waste according to claim 1, wherein the reactor additionally comprises a set of sensors and a control module.

* * * * *

SEQUENCE LISTING

```
Sequence total quantity: 3
SEQ ID NO: 1          moltype = AA  length = 727
FEATURE               Location/Qualifiers
source                1..727
                      mol_type = protein
                      organism = Nitrosomonas aestuarii
SEQUENCE: 1
MPILRVALNI PLDTLFDYIA PNACEADIGL RVCVPFGKKK LTGVILEVCS DTEVPPEKLK  60
SVICIFRETP PLSAELLALF SFCSDYYHHP LGMVVMNSLP GKLRNNKPVS LKVHVNRDQF  120
VLSAAGRQVD TSTIPARNTL MHRLLATLKS TPSLNARDVR KISPRADHIL QDWVRKGWVD  180
IIPETDPAVA TPALPELTSE QSTAVGVIAA KLDRFDTWVL HGVTGSGKTE VYLRLIAQTL  240
SKGKQALVLI PEISLTPQLE SVFRERFIMT RIVSLHSGLN DSERLSGWLQ AQQGEAGVVL  300
GTRLAVFTPL PKLGLIIVDE EQDSSFKQQD GLRYSARDLA IFRASQAHIP VVLGSATPSL  360
ESYYNVLNDR YRYLRLKNRA IKNAVLPQVK CIDLRSEKPL NGLSIPLIKA IDACLAHRQQ  420
CLIFINRRGY APVLLCKSCG WTAVCQRCTS RLVVHLQDKK LSCHHCGYLE SFPHACPQCG  480
DQDMMPFGRG TQRVEEALAI RFPSARILRI DRDSTRRKNA WQAILRSVHQ HEVDILVGTQ  540
LLAKGHDFPN LSLVGILGSD ISLYSTDFRA GERLFTQLMQ VAGRAGRAKI SGSVLIQTEF  600
PNHPLYQALQ RHDYDVLAKT ILAERKMAGF PPYVYQALLR AEAHSLKKVL DFLDTAHKLT  660
QSLTGIEVFD PVPAHMARLK GMERAHLLVQ SGSRKKLQIF LAQWYKQLSA LTAHKVRWSL  720
DVDPIEF                                                            727

SEQ ID NO: 2          moltype = AA  length = 468
FEATURE               Location/Qualifiers
source                1..468
                      mol_type = protein
                      organism = synthetic construct
SEQUENCE: 2
MQYLPIFLNI RGQQCLVVGG GTVAVRKVAL LRQAGAEVKV IAPKLHEQLQ EWADKGKITA  60
QQASFSETEI KSCYLVIAAT DDSSLNEQVY HLATAQGVLV NVADCPRFCD FILPSIVDRS  120
PVIVAVSSGG ASPVLARLLR ARLETLIPQA YGRLGQFAAR YRSRIKQRIT GIRARRIFWE  180
KVLQGSIAER IFAGQEEEAE GALEAALEGG FVPEQGEVYL VGAGPGDPDL LTFRALRLMQ  240
QADVVFHDRL VSPEVLALVR REAERIYVGK KRSWHAVRQE EINMMLVRSA REGKRVLRLK  300
GGDPFIFGRG GEEIATLAAE NIPFQVVPGI TAASGCASYA GIPLTHRDHA HACIFVTGQL  360
KEGRLSLNWQ ALVQPQQTIV VYMGLSGLEI LCQELIAHGM PAVTPAALVQ QGTTSRQRVL  420
TGTLATLPDI VQGEDIHAPT LVIIGGVVAL YPQLAWFKVP DREPLDAR               468

SEQ ID NO: 3          moltype = AA  length = 452
FEATURE               Location/Qualifiers
source                1..452
                      mol_type = protein
                      organism = Nitrobacter winogradskyi
```

-continued

```
SEQUENCE: 3
MSGRNCLTIV LAAGEGTRMR SSLPKVLHPV GGQTLLSHVL AAAPGGPGTS LTVVIGPGHQ  60
AVADEAKRVR PDVMTFVQDE RLGTAHAVLA AKEAIIRGAD DLLIAFGDTP LISADTFARM  120
RAPLRAGASL AVLGFHARDP AGYGRLIVTD GRLTAIREDA DASPEERRMT LCNAGVMAFD  180
GRTALRIIEK IGNANSKGEY YLTDAVGLVA ELGLTAAVIE TGEDEVRGIN TKAQLAEAEQ  240
VMQARLRKAA LDAGVTMVAP ETVFLSADTS FGRDVTIEPY VIIGQGVTIA DGAVVHAFSH  300
LVQASIGRNA SVGPYARLRP GTSVGDGARI GNFVETKAAV LEAGAKVNHL TYIGDAHVGA  360
KANIGAGTIT CNYDGFNKHR TEIGEGAFVG SNSSLVAPLR IGAGAYIGSG SVVTKNVPDD  420
ALAVGRGQQT LREGWAKRFR EMKLLARKQK TG                               452
```